US009474782B2

(12) United States Patent
Kichler et al.

(10) Patent No.: US 9,474,782 B2
(45) Date of Patent: Oct. 25, 2016

(54) USE OF DECORIN FOR INCREASING MUSCLE MASS

(71) Applicant: Association Francaise contre les Myopathies, Paris (FR)

(72) Inventors: Antoine Kichler, Mennecy (FR); Daniel Scherman, Paris (FR)

(73) Assignee: Association Francaise contre les Myopathies, Paris (FR)

( * ) Notice: Subject to any disclaimer, the term of this patent is extended or adjusted under 35 U.S.C. 154(b) by 0 days.

(21) Appl. No.: 13/784,237

(22) Filed: Mar. 4, 2013

(65) Prior Publication Data

US 2013/0236426 A1  Sep. 12, 2013

Related U.S. Application Data

(62) Division of application No. 13/257,127, filed as application No. PCT/FR2010/050491 on Mar. 18, 2010, now abandoned.

(30) Foreign Application Priority Data

Mar. 18, 2009  (FR) ..................................... 09 01260

(51) Int. Cl.
   *A61K 38/17*  (2006.01)
   *A61K 45/06*  (2006.01)

(52) U.S. Cl.
   CPC ........... *A61K 38/1709* (2013.01); *A61K 45/06* (2013.01)

(58) Field of Classification Search
   None
   See application file for complete search history.

(56) References Cited

U.S. PATENT DOCUMENTS

| 5,705,609 A * | 1/1998 | Ruoslahti et al. |
| 2005/0020491 A1 | 1/2005 | Hook et al. |
| 2012/0058955 A1 | 3/2012 | Kichler et al. |

FOREIGN PATENT DOCUMENTS

| WO | WO 96/25178 A1 | 8/1996 |
| WO | WO 99/54491 A1 | 10/1999 |
| WO | WO 2005/094446 A2 | 10/2005 |
| WO | WO 2007/123848 A2 | 11/2007 |

OTHER PUBLICATIONS

Sato et al., Improvement of muscle healing through enhancement of muscle regeneration and prevention of fibrosis. Muscle Nerve, 28:365-372, 2003.*
Fukushimaet al., "The use of an antifibrosis agent to improve muscle recovery after laceration," Am. J. of Sports Med., 29(4):394-402, 2001.*
Lawlor MW, Viral gene therapy in skeletal muscle: a work in progress, J. Genet. Syndr. Gene Ther. 3:e109, 2012.*
Jackson et al., Designing nonviral vectors for efficient gene transfer and long-term gene expression, Mol. Ther. 14(5):613-626, Nov. 2006.*
Evans, WJ, Skeletal muscle loss: cachexia, sarcopenia, and inactivity, Am. J. Clin. Nutr. 91(supp1)1123S-1127S, 2010.*
Wang et al., Sustained AAV-mediated dystrophin expression in a canine model of Duchenne Muscular Dystrophy with a brief course of immunosuppression, Mol. Ther. 1596):1160-1166, Jun. 2007.*

(Continued)

*Primary Examiner* — Claire Kaufman
(74) *Attorney, Agent, or Firm* — Wolf, Greenfield & Sacks, P.C.

(57) ABSTRACT

The invention concerns decorin for increasing muscle mass, particularly in the treatment of muscular dystrophies.

20 Claims, 2 Drawing Sheets

(56) References Cited

OTHER PUBLICATIONS

Genetic Home Reference [online]. MSTN. Dec. 1, 2014 [retrieved on Dec. 9, 2014]. Retrieved the Internet: <http://ghr.nlm.nih.gov/gene/MSTN>.*
Zhu et al., Relationships between transforming growth factor-beta1, myostatin, and decorin: implications for skeletal muscle fibrosis, J. Biol. Chem. 282(35):25852-25863, Aug. 31, 2007 (electronic publication date Jun. 27, 2007).*
McPherron et al., Regulation of skeletal muscle mass in mice by a new TGF-β superfamily member, Nat. 387:83-90, May 1997.*
International Search Report for PCT/FR2010/050491, mailed Jul. 2, 2010.
International Preliminary Report on Patentability for PCT/FR2010/050491, mailed Sep. 29, 2011.
Office Communication, mailed Jun. 8, 2012 for U.S. Appl. No. 13/257,127.
Genbank Submission; NIH/NCBI, Accession No. NM_001920.3; Iozzo et al.; Dec. 11, 2011.
Genbank Submission; NIH/NCBI, Accession No. NM_133503.2, Iozzo et al.; Dec. 11, 2011.
Genbank Submission; NIH/NCBI, Accession No. NM_133504.2, Iozzo et al.; Dec. 11, 2011.
Genbank Submission; NIH/NCBI, Accession No. NM_133505.2, Iozzo et al.; Dec. 11, 2011.
Genbank Submission; NIH/NCBI, Accession No. NM_133506.2, Iozzo et al.; Dec. 11, 2011.
Genbank Submission; NIH/NCBI, Accession No. NM_133507.2, Iozzo et al.; Dec. 11, 2011.
Genbank Submission; NIH/NCBI, Accession No. NP_001911, Iozzo et al.; Dec. 11, 2011.
Genbank Submission; NIH/NCBI, Accession No. NP_598010.1, Iozzo et al.; Dec. 11, 2011.
Genbank Submission; NIH/NCBI, Accession No. NP_598011.1, Iozzo et al.; Dec. 11, 2011.
Genbank Submission; NIH/NCBI, Accession No. NP_598012.1, Iozzo et al.; Dec. 11, 2011.
Genbank Submission; NIH/NCBI, Accession No. NP_598013.1, Iozzo et al.; Dec. 11, 2011.
Genbank Submission; NIH/NCBI, Accession No. NP_598014.1, Iozzo et al.; Dec. 11, 2011.
Genbank Submission; Swiss-Prot, Accession No. P28654, Naitoh et al.; Nov. 16, 2011.
Ameye et al., Mice deficient in small leucine-rich proteoglycans: novel in vivo models for osteoporosis, osteoarthritis, Ehlers-Danlos syndrome, muscular dystrophy, and corneal diseases. Glycobiology. Sep. 2002;12(9):107R-16R.
Bertoni, Clinical approaches in the treatment of Duchenne muscular dystrophy (DMD) using oligonucleotides. Front Biosci. Jan. 1, 2008;13:517-27.
Dumonceaux et al., Combination of myostatin pathway interference and dystrophin rescue enhances tetanic and specific force in dystrophic mdx mice. Mol Ther. May 2010;18(5):881-7. Epub Jan. 26, 2010.
Fadic et al., Increase in decorin and biglycan in Duchenne Muscular Dystrophy: role of fibroblasts as cell source of these proteoglycans in the disease. J Cell Mol Med. Jul.-Sep. 2006;10(3):758-69.
Fakhfakh et al., Administration of a Soluble Activin Type Iib Receptor Promotes the Transplantation of Human Myoblasts in Dystrophic Mice. Cell Transplant. Mar. 22, 2010. [Epub ahead of print]. 31 pages.
Gosselin et al., Localization and early time course of TGF-β1 mRNA expression in dystrophic muscle. Muscle & Nerve. 2004;30(5):645-53.
Kishioka et al., Decorin enhances the proliferation and differentiation of myogenic cells through suppressing myostatin activity. J Cell Physiol. Jun. 2008;215(3):856-67.
Krusius et al., Primary structure of an extracellular matrix proteoglycan core protein deduced from cloned cDNA. Proc Natl Acad Sci U S A. Oct. 1986;83(20):7683-7.
Li et al., Decorin gene transfer promotes muscle cell differentiation and muscle regeneration. Mol Ther. Sep. 2007;15(9):1616-22. Epub Jul. 3, 2007.
McNally et al., Muscle diseases: the muscular dystrophies. Annu Rev Pathol. 2007;2:87-109.
Miura et al., Decorin binds myostatin and modulates its activity to muscle cells. Biochem Biophys Res Commun. Feb. 10, 2006;340(2):675-80. Epub Dec. 20, 2005.
Reed et al., The role of decorin in collagen fibrillogenesis and skin homeostasis. Glycoconj J. May-Jun. 2002;19(4-5):249-55.
Schönherr et al., Decorin core protein fragment Leu155-Val260 interacts with TGF-beta but does not compete for decorin binding to type I collagen. Arch Biochem Biophys. Jul. 15, 1998;355(2):241-8.
Verma et al., Gene therapy—promises, problems and prospects. Nature. Sep. 18, 1997;389(6648):239-42.
Yang et al., Decorin is a Zn2+ metalloprotein. J Biol Chem. Apr. 30, 1999;274(18):12454-60.
Zanotti et al., Altered extracellular matrix transcript expression and protein modulation in primary Duchenne muscular dystrophy myotubes. Matrix Biol. Oct. 2007;26(8):615-24. Epub Jun. 27, 2007.
Zanotti et al., Decorin and biglycan expression is differentially altered in several muscular dystrophies. Brain. Nov. 2005;128(Pt 11):2546-55. Epub Sep. 23, 2005.
Zhu et al., Relationships between transforming growth factor-beta1, myostatin, and decorin: implications for skeletal muscle fibrosis. J Biol Chem. Aug. 31, 2007;282(35):25852-63. Epub Jun. 27, 2007.
Biswas et al., Oligomerization of a MutS mismatch repair protein from *Thermus aquaticus*. J Biol Chem. Aug. 13, 1999;274(33):23673-8.
Guiraud et al., Identification of decorin derived peptides with a zinc dependent anti-myostatin activity. Neuromuscul Disord. Dec. 2012;22(12):1057-68. doi: 10.1016/j.nmd.2012.07.002. Epub Jul. 31, 2012.
Hausser et al., Selective inactivity of TGF-beta/decorin complexes. FEBS Lett. Oct. 24, 1994;353(3):243-5.
McEwan et al., Structural correlations in the family of small leucine-rich repeat proteins and proteoglycans. J Struct Biol. Aug. 2006;155(2):294-305. Epub May 19, 2006.
Murphy et al., Antibody-directed myostatin inhibition enhances muscle mass and function in tumor-bearing mice. Am J Physiol Regul Integr Comp Physiol. Jun. 2011;301:R716-R726.
Schaefer et al., Biological functions of the small leucine-rich proteoglycans: from genetics to signal transduction. J Biol Chem. Aug. 1, 2008;283(31):21305-9. doi: 10.1074/jbc.R800020200. Epub May 6, 2008.
Tsuchida, Targeting myostatin for therapies against muscle-wasting disorders. Curr Opin Drug Discov Devel. Jul. 2008;11(4):487-94.
Whittemore et al., Inhibition of myostatin in adult mice increases skeletal muscle mass and strength. Biochem Biophys Res Commun. Jan. 24, 2003;300(4):965-71.
Wolfman et al., Activation of latent myostatin by the BMP-1/tolloid family of metalloproteinases. Proc Natl Acad Sci U S A. Dec. 23, 2003;100(26):15842-6. Epub Dec. 11, 2003.
Zhu et al., Myostatin signaling through Smad2, Smad3 and Smad4 is regulated by the inhibitory Smad7 by a negative feedback mechanism. Cytokine. Jun. 21, 2004;26(6):262-72.

* cited by examiner

USE OF DECORIN FOR INCREASING MUSCLE MASS

RELATED APPLICATIONS

The present application is a divisional of and claims priority under 35 U.S.C. §120 to U.S. patent application Ser. No. 13/257,127, filed Nov. 8, 2011, which is a national stage filing under 35 U.S.C. §371 of international PCT application, PCT/FR2010/050491, filed Mar. 18, 2010, which claims priority to French application, no. 0901260, filed Mar. 18, 2009, each of which is incorporated herein by reference.

TECHNICAL DOMAIN

The aim of this invention is to increase muscle mass in humans or animals.

More specifically, it advocates the use of decorin to develop muscle mass, particularly for treating pathological conditions associated with muscular wasting, such as muscular dystrophy.

PRIOR STATE OF THE ART

Neuromuscular diseases include various conditions that are generally associated with temporary or permanent loss of muscular strength. This loss of strength is usually accompanied by muscular wasting, also known as amyotrophia.

Myopathies, which involve damage to the actual muscle fibres, are an important group of these muscular diseases, and among them, progressive muscular dystrophies are characterised by a decrease in muscular strength, generally with atrophy of the muscles, as well as abnormalities in the muscle biopsy showing modifications of the tissue. This group notably includes Duchenne muscular dystrophy (or DMD), Becker muscular dystrophy (or BMD) and the limb girdle muscular dystrophies.

Associated genetic abnormalities have been identified for some of these diseases. Duchenne or Becker muscular dystrophies are related to alterations in the gene encoding dystrophin, type 2A limb girdle muscular dystrophy (LGMD 2A or calpainopathy) to alterations in the calpain 3 gene, while the sarcoglycanopathies or the dystrophy types LGMD 2C, LGMD 2D, LGMD 2E, LGMD 2F are related to defects in the γ-, α-, β- and δ-sarcoglycan genes respectively (McNally E M, Pytel P, *Muscle diseases: the muscular dystrophies*. Annu Rev Pathol. 2007; Vol 2: 87-109).

In these particular cases, different gene therapy strategies are being developed but are difficult to put into practice.

Nevertheless and more generally in all cases of muscular wasting, there is a clear need to develop technical solutions to increase muscle mass and/or volume.

The document WO 2005/094446 identified antibodies against an epitope located between residues 40 and 64 of mature human myostatin which could increase muscle mass. However, this strategy based on the recognition of myostatin by an antibody is not free of problems. Alternative solutions therefore need to be found.

The present invention is based on the discovery by the inventors of this property of decorin.

Decorin belongs to the SLRP (Small Leucine-Rich Proteoglycan) family of proteins and includes an LRR (Leucine-Rich Repeat) segment. Decorin is a member of class I of the SLRPs. The members of this family are secreted with a propeptide which, in some cases, is cleaved. Decorin also has a glycosaminoglycan (GAG) chain.

Decorin is a protein of the extracellular matrix, with a similar structure to that of the protein biglycan. It plays a role in assembling the matrix and interacts with various partners, such as type I, II, III and IV collagen, or TGF-beta (Ameye L, Young M F, *Mice deficient in small leucine-rich proteoglycans: novel in vivo models for osteoporosis, osteoarthritis, Ehlers-Danlos syndrome, muscular dystrophy, and corneal diseases*. Glycobiology 2002; Vol 12:107 R-116R; Reed C C, Iozzo R V, *The role of decorin in collagen fibrillogenesis and skin homeostasis*. Glycoconj J. 2002; Vol 19 (4-5): 249-55).

On the basis of its interaction with TGF-beta, WO 96/25178 proposed the use of decorin to treat diseases associated with tissue fibrosis, i.e. excessive production of extracellular matrix, without relating this to the muscle mass problem.

DETAILED DESCRIPTION OF THE INVENTION

The present invention thus concerns the use of decorin to counter muscle wasting and even to increase muscle mass.

For this invention, the term "muscle mass" could be replaced either by muscle weight or volume.

More precisely the invention also concerns:
- a composition containing decorin to treat diseases associated with muscle wasting;
- the use of decorin in the preparation of a medicinal product for treating diseases associated with muscle wasting;
- a composition containing decorin to increase muscle mass;
- the use of decorin to increase muscle mass.

There are a number of conditions in which muscle wasting occurs.

Firstly, it may result from pathological conditions, particularly in the case of neuromuscular diseases. Duchenne muscular dystrophy is a disease particularly targeted, but all forms of neuromuscular diseases, especially muscular dystrophies, can be treated.

In addition, cachexia or marasmus is also a medical condition targeted by this invention. This state is characterized by extreme thinness, especially of the muscles, caused by prolonged illness or inadequate calorie or protein intake.

This condition is particularly seen in cases of chronic diseases such as cancer or AIDS or in individuals with either heart failure, where there is atrophy of skeletal muscles in 68% of patients, or urinary incontinence.

Although not actually considered as pathological, some situations are associated with muscle wasting: ageing, prolonged immobilisation etc. Here again, therefore, there is a reason for increasing the muscle mass.

The invention also offers the possibility particularly in the area of food production of increasing animal meat production. The use of decorin is therefore of particular interest in animals.

This invention is based therefore on detection of the stimulating properties of decorin, particularly related to muscle volume.

In the invention, "decorin" is used generically to mean the protein described by Krusius et al. (Krusius T., Ruoslahti E., *Primary structure of an extracellular matrix proteoglycan core protein deduced from cloned cDNA*. Proc Natl Acad Sci USA 1986; Vol 83 (20): 7683-87). The human protein described in this document has the sequence SEQ ID NO: 1. It is in the form of a preproprotein of 359 amino acids. Both native proteins and those deprived of their propeptide and/or their signal sequence (329 aa), are covered by this invention.

Although decorin naturally has a glycosaminoglycan (GAG) chain, a decorin without GAG (GAG−) can also be used in the context of this invention. This can, for example, be obtained by enzyme treatment.

The decorin can be obtained from any organism, but in this invention, decorin of human origin is preferred. More generally and advantageously, the protein comes from the same organism as the organism into which it will be administered. Preferably therefore, for therapeutic indications in humans, human decorin is used to advantage.

One of the primary benefits indeed of the solution proposed in this invention is that decorin is a protein naturally present in mammals, especially humans, and therefore a priori is not likely to cause side effects or immune responses.

It has also been shown for human decorin that transcriptional variants exist (variants b, c, d and e), resulting in protein isoforms, of sequence SEQ ID NO: 2, 3, 4 and 5, respectively, included in this submission.

In the context of the invention, the term "decorin" thus has a wide meaning and covers:
  the native protein, particularly the sequence SEQ ID NO: 1;
  the protein with or without the GAG chain (GAG+ or GAG−, respectively);
  the protein lacking the propeptide and/or the signal sequence;
  variants of these proteins, especially embodied in the sequences SEQ ID NOS: 2 to 5;
  more generally active fragments of these proteins,
  or active derivatives or functional equivalents.

As far as the fragments or derivatives are concerned, they are, of course, active fragments or derivatives. The activity in question which these fragments or derivatives must possess concerns the ability to increase muscle mass, which is easily assessed by using the test described in this submission.

In practice, they are to advantage 60% identical to one of sequences SEQ ID NO: 1 to 7, even more advantageously 70%, 80% or 90% identical.

Thus, by way of example for the derivatives, it could be sequence SEQ ID NO: 6 corresponding to the murine protein of 354 aa, which is 80% identical to the human sequence SEQ ID NO: 1.

According to a preferred embodiment of the invention, the decorin is in the form of an active fragment. To advantage by "fragment" we mean a peptide containing less than 100 amino acids, to even greater advantage, less than 50 amino acids.

The use of a peptide instead of the protein has certain advantages, particularly in terms of its production but also concerning the possible risk of undesirable interference in vivo.

It has been shown as part of this application that a 41 residue fragment of the N-terminal part of murine decorin (SEQ ID NO: 7) corresponding to residues 31-71 of the sequence SEQ ID NO: 6, reported to fix zinc (Yang V W, LaBrenz S R, Rosenberg L C, McQuillan D, Hook M. Decorin is a Zn2+ metalloprotein. J Biol Chem. 1999, 274 (18): 12454-60), had the required activity. It has also been shown that an even smaller fragment of 30 residues (residues 42 to 71 of the sequence SEQ ID NO: 6 corresponding to SEQ ID NO: 15) was also active.

The corresponding domain, present in human decorin, can be easily determined by the methodology described in this document. Such a fragment may for example have the sequence SEQ ID NO: 16.

More generally, the invention therefore concerns the use of a fragment of decorin including the zinc binding domain, in practice the residues 31 to 71, possibly 42 to 71 of the murine sequence. In a particular embodiment, the sequence of the fragment in question corresponds to sequence SEQ ID NO: 7 or SEQ ID NO: 15. In addition, fragments which are to advantage 50% identical to SEQ ID NO: 7 or 15, or even more advantageously 60%, 70%, 80% or 90% identical to them, and which retain their ability to bind zinc, are also covered by this invention.

In addition, decorin, its fragments and active derivatives may also be in the form of fusion proteins or chimeric proteins with another protein fragment at their N- or C-terminal ends, which can, for example, but without being limited to this, increase the residence time of the protein in the organism. A preferred example is the chimera consisting of the constant region of mammalian IgGs, attached via a hinge sequence to decorin or one of its fragments. Another example is human or mammalian albumin, also attached to decorin or to a protein fragment of decorin. Such combinations can be obtained both from a recombinant cDNA and by chemical bonding of the 2 proteins.

The present invention is therefore based on an exogenous supply of decorin. In fact, the composition covered by the invention consists of either the protein as such or a system producing the protein.

As far as the protein itself is concerned, it could be either native decorin, purified from an organism naturally producing this protein, or a recombinant protein produced by any of the synthesis systems available and known to those working in the field.

Alternatively, a nucleic acid sequence encoding decorin is put into an expression system, to advantage under the control of a promoter in a vector. After introduction into the body, the decorin is produced in vivo. The transfer of the nucleic acids (DNA or RNA) can be done either with viral approaches to gene transfer (e.g. adeno-associated virus or AAV) or with non-viral approaches (e.g. by simple intramuscular injection of a plasmid). Genomic DNA may be of interest since in some cases, the presence of introns stabilises the prespliced mRNA and improves its stability in the nucleus and its export, which leads to better protein expression.

Decorin, its derivatives or fragments, can thus be provided in the form of nucleic acids, particularly DNA or RNA, and may for example be in the form of transcripts occurring naturally in humans or the mouse. The following sequences are preferred:
  Sequence SEQ ID NO: 8, corresponding to the A1 variant (Accession Number NM_001920.3), which is the longest transcript and encodes the isoform a of the human decorin sequence SEQ ID NO: 1 (Accession Number NP_001911);
  Sequence SEQ ID NO: 9, corresponding to the A2 variant (Accession Number NM_133503.2), which uses an alternative exon at the 5′UTR compared with the variant A1 and encodes the same protein sequence SEQ ID NO: 1 (Accession Number NP_598010.1);
  Sequence SEQ ID NO: 10, corresponding to the B variant (Accession Number NM_133504.2), which lacks exons 3 and 4 in the coding region, compared with the A1 variant. This causes no change in reading frame but codes for an isoform b of the protein, which lacks an internal fragment of 109 aa, and has the sequence SEQ ID NO: 2 (Accession Number NP_598011.1);

Sequence SEQ ID NO: 11, corresponding to the C variant (Accession Number NM_133505.2), which lacks exons 3, 4 and 5 in the coding region, compared with the A1 variant. This causes a change of internal reading frame and the isoform c encoded of SEQ ID NO: 3 (Accession Number NP_598012.1) is shorter than isoform a by 147 amino acids;

Sequence SEQ ID NO: 12, corresponding to the D variant (Accession Number NM_133506.2), which lacks exons 4, 5, 6 and 7 in the coding region, compared with the A1 variant. This causes no change in reading frame but codes for an isoform d of the protein, which lacks an internal fragment of 187 aa, and has the sequence SEQ ID NO: 4 (Accession Number NP_598013.1);

Sequence SEQ ID NO: 13, corresponding to the E variant (Accession Number NM_133507.2), which lacks exons 3, 4, 5, 6 and 7 in the coding region, compared with the A1 variant. This causes a change of internal reading frame and the isoform e encoded of SEQ ID NO: 5 (Accession Number NP_598014.1) is shorter than isoform a by 284 amino acids;

Sequence SEQ ID NO: 14, encoding the murine protein sequence SEQ ID NO: 6 (Accession Number P28654).

As already mentioned, decorin is known to be a zinc metalloprotein. Owing to this and in order to potentiate its activity, one could choose to provide additional zinc to that naturally available in the organism to which the decorin is administered. Thus, according to this embodiment, the composition containing the decorin also includes zinc, e.g. as zinc chloride, preferably at a concentration between 1 and 50 µM, even equal to 15 µM.

A composition containing decorin according to the invention for the treatment of diseases associated with muscle wasting or intended to increase muscle mass may also contain any acceptable compound or excipient, particularly a pharmaceutical compound or excipient. The route of administration may be intramuscular or intravenous, or even subcutaneous, intraperitoneal or oral.

To promote the engraftment of precursor cells or stem cells, it may be advantageous to combine the administration of decorin with the cell grafts (myoblasts, stem cells etc.). This administration can be simultaneous or separated in time.

It can also be advantageous to combine gene therapy for the treatment of a neuromuscular disease with administration of decorin. In a preferred embodiment, a therapeutic gene is associated with decorin treatment. Administration of the two treatments can be simultaneous or separated in time.

The beneficial effects of decorin result in an increase in muscle volume (either mass or weight), due to an increase in the area of fibres possibly associated with an increase in the number of fibres. These positive effects can be observed in the various different skeletal muscles, both in an organism with a disease affecting its muscle mass and in a healthy individual. In principle, there are no side effects and no immune reaction.

EXAMPLES OF EMBODIMENTS

The invention and the advantages resulting from it are better illustrated by the following examples of embodiments and the attached figures. These are in no way limiting.

The invention is further illustrated by means of recombinant mouse decorin injected intramuscularly into mdx mice with a gene encoding an altered dystrophin and serving as an experimental model of Duchenne muscular dystrophy, and gamma-sarcoglycan −/− mice (mouse model of sarcoglycanopathies on a pure C57/B16 background).

I) MATERIALS AND METHODS

Preparing the mDecorin Solution

The protein used was recombinant mouse decorin (mDecorin) of sequence SEQ ID NO: 6, provided by R&D Systems.

Twenty-four to forty hours before the injection, 100 µl of 150 mM sterile NaCl and 6 µl of 250 µM $ZnCl_2$ were added to 100 µg of mDecorin powder. The final volume was 106 µl with a final concentration of approximately 1 µg/µl. For the injections into the control muscles a mixture was also prepared of 100 µl of 150 mM NaCl and 6 µl of 250 µM $ZnCl_2$. All these solutions, after being vortexed, were stored at 4° C.

In Vivo Injection

All the mice were treated according to EU directives on human health and the use of experimental animals.

mdx dystrophic (S-linked muscular dystrophy) or gamma-sarcoglycan −/− mice were used that were at least 6 weeks old. 20 µg of mDecorin, i.e. 22 µl of the solution described above (20 µg Decorin+15 µM $ZnCl_2$/22 µl NaCl), were injected into the left tibialis anterior (LTA), the muscle treated. 22 µl of the control solution described above (15 µM $ZnCl_2$/22 µl NaCl) were administered into the control muscle, the right tibialis anterior (RTA). A specific number of days after injection, the mice were sacrificed and the RTA and LTA were removed, weighed then frozen for further histological study.

Preparation and Injection of the Solution Containing the Peptide mDCN 31-71:

The peptide with the sequence SEQ ID NO: 7 was synthesised by the company NeoMPS with purity >65%. It was dissolved at 2 mg/ml in 150 mM NaCl and stored at −80° C.

For injections, the preparation protocol was identical to that used for the protein, i.e. 24-40 hours before injection, the desired amount of peptide was removed from the stock solution and mixed with a solution of zinc chloride ($ZnCl_2$) and 150 mM NaCl, to produce a final zinc concentration of 15 µM. The injection protocol was identical to that used for the protein.

Histological Analyses

Laminin Labelling:

Cryostat sections (8 µm) were made of treated and control muscles using standard techniques. The slides were fixed with Dakopen (DAKO®, ref.: S 2002) for 10 minutes open to the air and then blocked with a solution of PBS/10% goat serum for 30 min at room temperature in a humidity chamber. The rabbit anti-laminin antibody (DAKO®, ref.: Z0097) was applied to the slides at a dilution of 1:1000 for 12 hours in the humidity chamber. The slides were then rinsed in PSB (5 minutes) while being agitated and the secondary antibody (Envision HRP rabbit kit) was applied to the slides in a humidity chamber for 30 min at room temperature. After rinsing the slides in PBS (5 minutes) while being agitated, the DAB (DAKO®, ref.: K 3466) was applied to the sections for 2 to 5 minutes at room temperature in a humidity chamber. The slides were rinsed constantly and were mounted in the fume cupboard. The results were analysed using ELLIX software.

HPS Staining:

Cryostat sections (8 μm) were made of treated and control muscles using standard techniques. The slides were immersed in Harris haematoxylin for 3 minutes and then rinsed with running water. The slides were then put into acid alcohol, rinsed and soaked in Scott's tap water substitute for one minute. After rinsing, the slides were immersed in phloxine for 30 seconds, rinsed with running water and soaked in absolute alcohol for one minute. After exposure to the saffron for 3 minutes, the slides were rinsed with absolute alcohol and mounted with Eukitt resin, the solvent for which is xylene. The results were analysed using the CARTHOGRAPH program.

II) RESULTS

1/Weight of Muscles at Different Times after Injection into Dystrophic mdx Mice:

The RTA and LTA muscles were collected 7 (D7), 14 (D14) or 21 (D21) days after the injection and weighed. The experiment was repeated on three separate mice each time. The results are summarised in the following tables:

Day 7:

| Mouse | Muscles | Weight (g) | Growth in % (100*LTA/RTA) − 100 |
| --- | --- | --- | --- |
| Mouse 1 | RTA 1 | 0.0661 | 3.18 |
|  | LTA 1 | 0.0682 |  |
| Mouse 2 | RTA 2 | 0.0774 | 0.90 |
|  | LTA 2 | 0.0781 |  |
| Mouse 3 | RTA 3 | 0.0749 | 2.94 |
|  | LTA 3 | 0.0771 |  |

Day 14:

| Mouse | Muscles | Weight | Growth |
| --- | --- | --- | --- |
| Mouse 4 | RTA 4 | 0.0707 | 58.98 |
|  | LTA 4 | 0.1124 |  |
| Mouse 5 | RTA 5 | 0.0694 | 48.41 |
|  | LTA 5 | 0.103 |  |
| Mouse 6 | RTA 6 | 0.0854 | 6.67 |
|  | LTA 6 | 0.0911 |  |

Day 21:

| Mouse | Muscles | Weight | Growth |
| --- | --- | --- | --- |
| Mouse 7 | RTA 7 | 0.068 | 53.09 |
|  | LTA 7 | 0.1041 |  |
| Mouse 8 | RTA 8 | 0.0567 | 66.31 |
|  | LTA 8 | 0.0943 |  |
| Mouse 9 | RTA 9 | 0.0731 | 37.21 |
|  | LTA 9 | 0.1003 |  |

Figure 1:
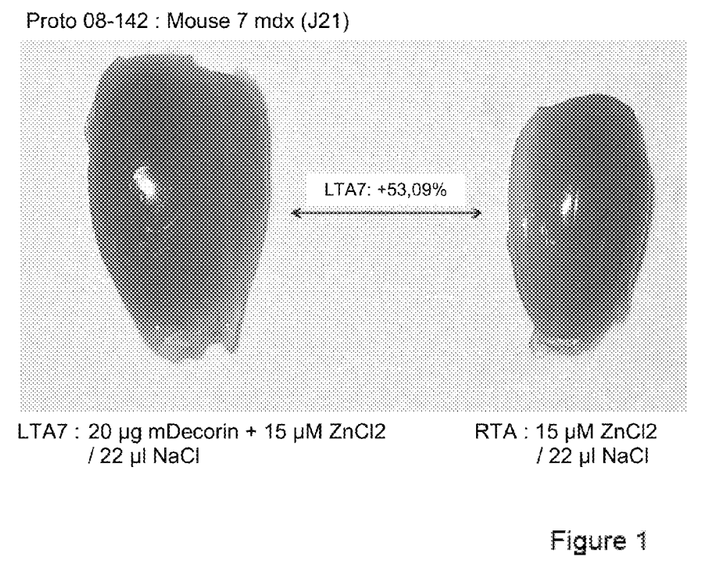
FIG. 1 is a view of the tibialis anterior muscle taken from mdx mouse 7 that had received (on the left) or not (on the right) an intramuscular injection of decorin.
Figure 2:
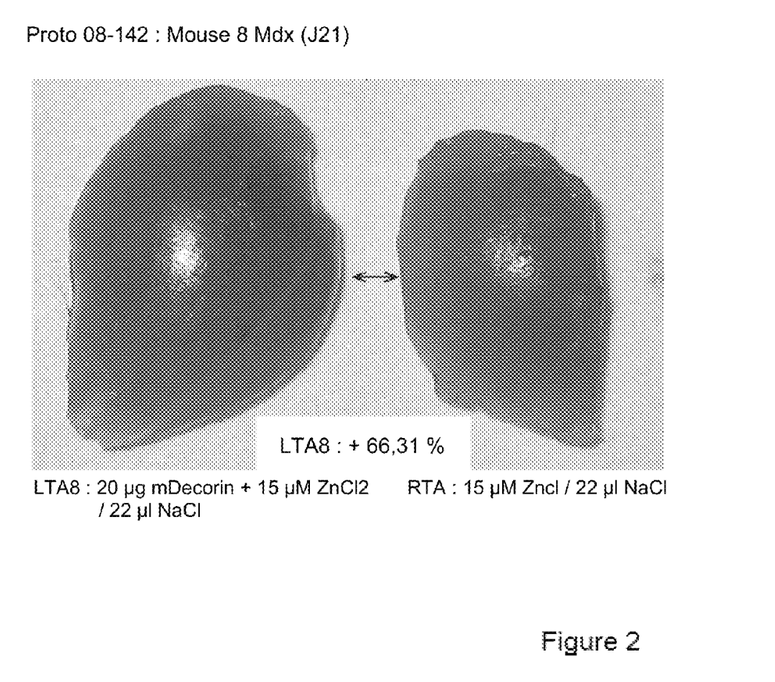
FIG. 2 is a view of the tibialis anterior muscle taken from mdx mouse 8 that had received (on the left) or not (on the right) an intramuscular injection of decorin.

The difference in muscle mass at day 21 between an mdx mouse that had received or had not received an intramuscular injection of decorin can be seen in FIGS. 1 and 2 for mice 7 and 8, respectively. There is a clear increase in muscle mass (+53.09% and +66.31%, respectively).

Figure 3:
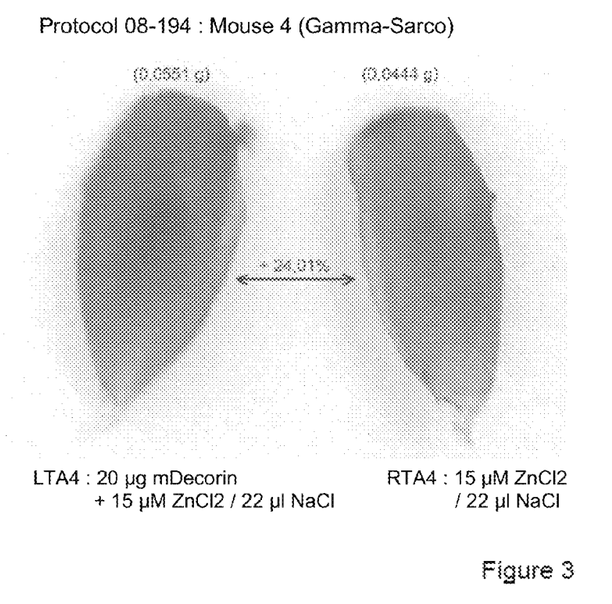
FIG. 3 is a view of the tibialis anterior muscle taken from gamma-sarcoglycan −/− mouse 4 at D18 that had received (on the left) or not (on the right) an intramuscular injection of decorin.
Figure 4:
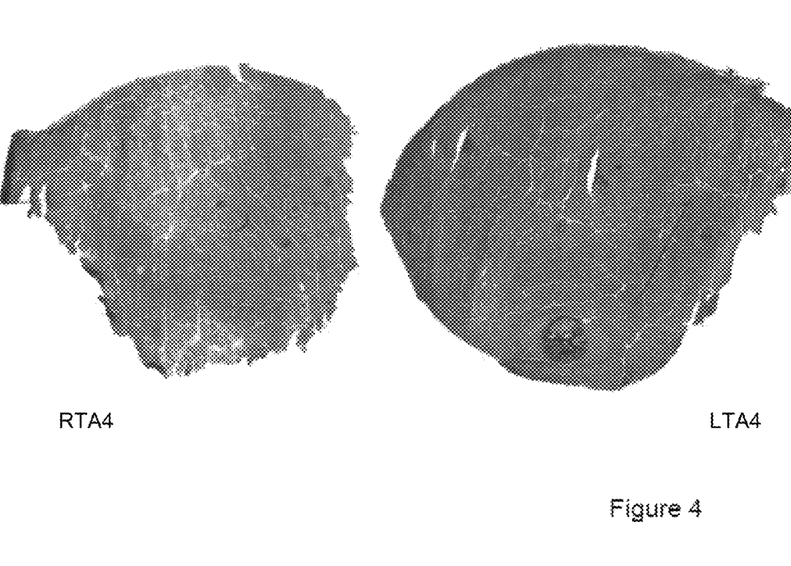
FIG. 4 is a view of a cross-section of the tibialis anterior muscle taken from gamma-sarcoglycan −/− mouse 4 at D18 that had received (LTA4 on the right of the figure) or not (RTA4 on the left of the figure) an intramuscular injection of decorin.

2/Weight of Muscles at D18 after Injection into Dystrophic Gamma-Sarcoglycan −/− Mice:

A second series of experiments was performed on four gamma-sarcoglycan −/− mice. The protocol was identical to that described for mdx mice. The mice were sacrificed on D18. The results, shown in FIGS. 3 and 4, are presented in the following table:

| Mouse | Muscles | Weight (g) | Growth |
| --- | --- | --- | --- |
| Mouse 1 | RTA 1 | 0.0456 | 10.75 |
|  | LTA 1 | 0.0505 |  |
| Mouse 2 | RTA 2 | 0.0413 | 17.43 |
|  | LTA 2 | 0.0485 |  |
| Mouse 3 | RTA 3 | 0.0528 | 12.31 |
|  | LTA 3 | 0.0593 |  |
| Mouse 4 | RTA 4 | 0.0444 | 24.10 |
|  | LTA 4 | 0.0551 |  |

3/Injection of the Peptide 31-71 Derived from the N-Terminal Part of Murine Decorin in mdx Mice:

To verify whether the N-terminal part of decorin is sufficient to produce observable increases in muscle mass, similar experiments were performed in the presence of the mDCN 31-71 peptide (SEQ ID NO: 7) corresponding to residues 31-71 of murine decorin (SEQ ID NO:6). This peptide has been described as being sufficient and necessary for binding zinc (Yang V W, LaBrenz S R, Rosenberg L C, McQuillan D, Höök M. *Decorin is a Zn2+ metalloprotein*. J Biol Chem. 1999, 274 (18): 12454-60).

mdx Mice were Injected Intramuscularly into the TA with the Following Formulations:

LTA 1: 65 μg peptide 41 DCN+15 μM ZnCl2/33 μl NaCl;

RTA 2: 15 μM ZnCl2/33 μl NaCl.

At D18, the mice were sacrificed and the weight of the RTA and LTA muscles was measured. The results are given in the following table:

|  | Muscle | Weight (mg) | Growth |
| --- | --- | --- | --- |
| Mouse 4 | RTA 4 | 53.6 | 8.77 |
|  | LTA 4 | 58.3 |  |
| Mouse 5 | RTA 5 | 39.2 | 19.39 |
|  | LTA 5 | 46.8 |  |
| Mouse 6 | RTA 6 | 40.1 | 24.69 |
|  | LTA 6 | 50 |  |

These results show that an effect on muscle growth is indeed maintained in the presence of just this part of decorin.

Similar results were obtained with an even shorter peptide of 30 amino acids, with the sequence SEQ ID NO:15.

The invention claimed is:

1. A method of treating a neuromuscular disease associated with muscle wasting, the method comprising:
    administering to a subject in need of treatment of the neuromuscular disease associated with muscle wasting a fragment of decorin consisting of the sequence of SEQ ID NO: 7, 15, or 16, wherein the amount of the fragment of decorin is sufficient to increase muscle mass in the subject.

2. The method of claim 1, wherein the fragment of decorin is administered by intramuscular, intraperitoneal, or intravenous injection.

3. The method of claim 1, wherein the fragment of decorin consists of the sequence of SEQ ID NO: 7.

4. The method of claim 1, wherein the fragment of decorin consists of the sequence of SEQ ID NO: 15.

5. The method of claim 1, wherein the fragment of decorin consists of the sequence of SEQ ID NO: 16.

6. The method of claim 1, wherein the neuromuscular disease associated with muscle wasting is muscular dystrophy.

7. The method of claim 6, wherein the muscular dystrophy is Duchenne muscular dystrophy.

8. The method of claim 3, wherein the neuromuscular disease associated with muscle wasting is muscular dystrophy.

9. The method of claim 8, wherein the muscular dystrophy is Duchenne muscular dystrophy.

10. The method of claim 4, wherein the neuromuscular disease associated with muscle wasting is muscular dystrophy.

11. The method of claim 10, wherein the muscular dystrophy is Duchenne muscular dystrophy.

12. The method of claim 5, wherein the neuromuscular disease associated with muscle wasting is muscular dystrophy.

13. The method of claim 12, wherein the muscular dystrophy is Duchenne muscular dystrophy.

14. The method of claim 3, wherein the subject is a human.

15. The method of claim 4, wherein the subject is a human.

16. The method of claim 5, wherein the subject is a human.

17. The method of claim 1 further comprising administering to the subject a zinc-containing agent.

18. The method of claim 3 further comprising administering to the subject a zinc-containing agent.

19. The method of claim 4 further comprising administering to the subject a zinc-containing agent.

20. The method of claim 5 further comprising administering to the subject a zinc-containing agent.

* * * * *

SEQUENCE LISTING

<160> NUMBER OF SEQ ID NOS: 16

<210> SEQ ID NO 1
<211> LENGTH: 359
<212> TYPE: PRT
<213> ORGANISM: artificial sequence
<220> FEATURE:
<223> OTHER INFORMATION: human DCN (variant A)

<400> SEQUENCE: 1

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
            100                 105                 110

Val Asn Asn Lys Ile Ser Lys Val Ser Pro Gly Ala Phe Thr Pro Leu
        115                 120                 125

Val Lys Leu Glu Arg Leu Tyr Leu Ser Lys Asn Gln Leu Lys Glu Leu
    130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
            180                 185                 190

Asn Gly Ala Phe Gln Gly Met Lys Lys Leu Ser Tyr Ile Arg Ile Ala
        195                 200                 205

Asp Thr Asn Ile Thr Ser Ile Pro Gln Gly Leu Pro Pro Ser Leu Thr
    210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
            260                 265                 270

Glu Leu His Leu Asp Asn Asn Lys Leu Thr Arg Val Pro Gly Gly Leu
        275                 280                 285

Ala Glu His Lys Tyr Ile Gln Val Val Tyr Leu His Asn Asn Asn Ile
    290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
            340                 345                 350

Ile Gln Leu Gly Asn Tyr Lys
        355

<210> SEQ ID NO 2
<211> LENGTH: 250
<212> TYPE: PRT
<213> ORGANISM: artificial sequence
<220> FEATURE:
<223> OTHER INFORMATION: human DCN (variant B)

<400> SEQUENCE: 2

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Glu Leu Gly Thr Asn Pro Leu Lys Ser Ser
65                  70                  75                  80

Gly Ile Glu Asn Gly Ala Phe Gln Gly Met Lys Lys Leu Ser Tyr Ile
                85                  90                  95

Arg Ile Ala Asp Thr Asn Ile Thr Ser Ile Pro Gln Gly Leu Pro Pro
            100                 105                 110

Ser Leu Thr Glu Leu His Leu Asp Gly Asn Lys Ile Ser Arg Val Asp
        115                 120                 125

Ala Ala Ser Leu Lys Gly Leu Asn Asn Leu Ala Lys Leu Gly Leu Ser
    130                 135                 140

Phe Asn Ser Ile Ser Ala Val Asp Asn Gly Ser Leu Ala Asn Thr Pro
145                 150                 155                 160

His Leu Arg Glu Leu His Leu Asp Asn Asn Lys Leu Thr Arg Val Pro
                165                 170                 175

Gly Gly Leu Ala Glu His Lys Tyr Ile Gln Val Val Tyr Leu His Asn
            180                 185                 190

Asn Asn Ile Ser Val Val Gly Ser Ser Asp Phe Cys Pro Pro Gly His
        195                 200                 205

Asn Thr Lys Lys Ala Ser Tyr Ser Gly Val Ser Leu Phe Ser Asn Pro
    210                 215                 220

Val Gln Tyr Trp Glu Ile Gln Pro Ser Thr Phe Arg Cys Val Tyr Val
225                 230                 235                 240

Arg Ser Ala Ile Gln Leu Gly Asn Tyr Lys
                245                 250

<210> SEQ ID NO 3
<211> LENGTH: 212
<212> TYPE: PRT
<213> ORGANISM: artificial sequence
<220> FEATURE:
<223> OTHER INFORMATION: human DCN (variant C)

<400> SEQUENCE: 3

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

```
Ala Ser Gly Ile Gly Pro Glu Val Pro Asp Asp Arg Asp Phe Glu Pro
         35                  40                  45

Ser Leu Gly Pro Val Cys Pro Phe Arg Cys Gln Cys His Leu Arg Val
 50                  55                  60

Val Gln Cys Ser Asp Leu Gly Leu Pro Pro Ser Leu Thr Glu Leu His
 65                  70                  75                  80

Leu Asp Gly Asn Lys Ile Ser Arg Val Asp Ala Ala Ser Leu Lys Gly
                 85                  90                  95

Leu Asn Asn Leu Ala Lys Leu Gly Leu Ser Phe Asn Ser Ile Ser Ala
             100                 105                 110

Val Asp Asn Gly Ser Leu Ala Asn Thr Pro His Leu Arg Glu Leu His
             115                 120                 125

Leu Asp Asn Asn Lys Leu Thr Arg Val Pro Gly Gly Leu Ala Glu His
 130                 135                 140

Lys Tyr Ile Gln Val Val Tyr Leu His Asn Asn Asn Ile Ser Val Val
145                 150                 155                 160

Gly Ser Ser Asp Phe Cys Pro Pro Gly His Asn Thr Lys Lys Ala Ser
                 165                 170                 175

Tyr Ser Gly Val Ser Leu Phe Ser Asn Pro Val Gln Tyr Trp Glu Ile
             180                 185                 190

Gln Pro Ser Thr Phe Arg Cys Val Tyr Val Arg Ser Ala Ile Gln Leu
             195                 200                 205

Gly Asn Tyr Lys
            210

<210> SEQ ID NO 4
<211> LENGTH: 172
<212> TYPE: PRT
<213> ORGANISM: artificial sequence
<220> FEATURE:
<223> OTHER INFORMATION: human DCN (variant D)

<400> SEQUENCE: 4

Met Lys Ala Thr Ile Ile Leu Leu Leu Leu Ala Gln Val Ser Trp Ala
 1               5                  10                  15

Gly Pro Phe Gln Gln Arg Gly Leu Phe Asp Phe Met Leu Glu Asp Glu
             20                  25                  30

Ala Ser Gly Ile Gly Pro Glu Val Pro Asp Asp Arg Asp Phe Glu Pro
         35                  40                  45

Ser Leu Gly Pro Val Cys Pro Phe Arg Cys Gln Cys His Leu Arg Val
 50                  55                  60

Val Gln Cys Ser Asp Leu Gly Leu Asp Lys Val Pro Lys Asp Leu Pro
 65                  70                  75                  80

Pro Asp Thr Thr Leu Leu Asp Leu Gln Asn Asn Lys Ile Thr Glu Ile
                 85                  90                  95

Lys Asp Gly Asp Phe Lys Asn Leu Lys Asn Leu His Val Val Tyr Leu
             100                 105                 110

His Asn Asn Asn Ile Ser Val Val Gly Ser Ser Asp Phe Cys Pro Pro
             115                 120                 125

Gly His Asn Thr Lys Lys Ala Ser Tyr Ser Gly Val Ser Leu Phe Ser
 130                 135                 140

Asn Pro Val Gln Tyr Trp Glu Ile Gln Pro Ser Thr Phe Arg Cys Val
145                 150                 155                 160

Tyr Val Arg Ser Ala Ile Gln Leu Gly Asn Tyr Lys
                 165                 170
```

-continued

```
<210> SEQ ID NO 5
<211> LENGTH: 75
<212> TYPE: PRT
<213> ORGANISM: artificial sequence
<220> FEATURE:
<223> OTHER INFORMATION: human DCN (variant E)

<400> SEQUENCE: 5

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Gly Cys Leu Pro Ser
65                  70                  75

<210> SEQ ID NO 6
<211> LENGTH: 354
<212> TYPE: PRT
<213> ORGANISM: artificial sequence
<220> FEATURE:
<223> OTHER INFORMATION: murine DCN

<400> SEQUENCE: 6

Met Lys Ala Thr Leu Ile Phe Phe Leu Leu Ala Gln Val Ser Trp Ala
1               5                   10                  15

Gly Pro Phe Glu Gln Arg Gly Leu Phe Asp Phe Met Leu Glu Asp Glu
            20                  25                  30

Ala Ser Gly Ile Ile Pro Tyr Asp Pro Asp Asn Pro Leu Ile Ser Met
        35                  40                  45

Cys Pro Tyr Arg Cys Gln Cys His Leu Arg Val Val Gln Cys Ser Asp
    50                  55                  60

Leu Gly Leu Asp Lys Val Pro Trp Asp Phe Pro Pro Asp Thr Thr Leu
65                  70                  75                  80

Leu Asp Leu Gln Asn Asn Lys Ile Thr Glu Ile Lys Glu Gly Ala Phe
                85                  90                  95

Lys Asn Leu Lys Asp Leu His Thr Leu Ile Leu Val Asn Asn Lys Ile
            100                 105                 110

Ser Lys Ile Ser Pro Glu Ala Phe Lys Pro Leu Val Lys Leu Glu Arg
        115                 120                 125

Leu Tyr Leu Ser Lys Asn Gln Leu Lys Glu Leu Pro Glu Lys Met Pro
    130                 135                 140

Arg Thr Leu Gln Glu Leu Arg Val His Glu Asn Glu Ile Thr Lys Leu
145                 150                 155                 160

Arg Lys Ser Asp Phe Asn Gly Leu Asn Asn Val Leu Val Ile Glu Leu
                165                 170                 175

Gly Gly Asn Pro Leu Lys Asn Ser Gly Ile Glu Asn Gly Ala Phe Gln
            180                 185                 190

Gly Leu Lys Ser Leu Ser Tyr Ile Arg Ile Ser Asp Thr Asn Ile Thr
        195                 200                 205

Ala Ile Pro Gln Gly Leu Pro Thr Ser Leu Thr Glu Val His Leu Asp
    210                 215                 220

Gly Asn Lys Ile Thr Lys Val Asp Ala Pro Ser Leu Lys Gly Leu Ile
225                 230                 235                 240
```

```
Asn Leu Ser Lys Leu Gly Leu Ser Phe Asn Ser Ile Thr Val Met Glu
                245                 250                 255

Asn Gly Ser Leu Ala Asn Val Pro His Leu Arg Glu Leu His Leu Asp
            260                 265                 270

Asn Asn Lys Leu Leu Arg Val Pro Ala Gly Leu Ala Gln His Lys Tyr
        275                 280                 285

Ile Gln Val Val Tyr Leu His Asn Asn Asn Ile Ser Ala Val Gly Gln
    290                 295                 300

Asn Asp Phe Cys Arg Ala Gly His Pro Ser Arg Lys Ala Ser Tyr Ser
305                 310                 315                 320

Ala Val Ser Leu Tyr Gly Asn Pro Val Arg Tyr Trp Glu Ile Phe Pro
                325                 330                 335

Asn Thr Phe Arg Cys Val Tyr Val Arg Ser Ala Ile Gln Leu Gly Asn
            340                 345                 350

Tyr Lys

<210> SEQ ID NO 7
<211> LENGTH: 41
<212> TYPE: PRT
<213> ORGANISM: artificial sequence
<220> FEATURE:
<223> OTHER INFORMATION: murine 31-71 DCN

<400> SEQUENCE: 7

Asp Glu Ala Ser Gly Ile Ile Pro Tyr Asp Pro Asp Asn Pro Leu Ile
1               5                   10                  15

Ser Met Cys Pro Tyr Arg Cys Gln Cys His Leu Arg Val Val Gln Cys
            20                  25                  30

Ser Asp Leu Gly Leu Asp Lys Val Pro
        35                  40

<210> SEQ ID NO 8
<211> LENGTH: 2305
<212> TYPE: DNA
<213> ORGANISM: artificial sequence
<220> FEATURE:
<223> OTHER INFORMATION: variant A1 human DCN

<400> SEQUENCE: 8
gaatctacaa taagacaaat ttcaaatcaa gttgctccac tatactgcat aagcagttta      60
gaatcttaag cagatgcaaa aagaataaag caaatgggag gaaaaaaaag gccgataaag     120
tttctggcta caatacaaga gacatatcat taccatatga tctaatgtgg gtgtcagccg     180
gattgtgttc attgagggaa acctttatttt ttaactgtgc tatggagtag aagcaggagg    240 tttcaacct agtcacagag cagcacctac cccctcctcc tttccacacc tgcaaactct     300
tttacttggg ctgaatattt agtgtaatta catctcagct ttgagggctc ctgtggcaaa    360
ttcccggatt aaaaggttcc ctggttgtga aaatacatga gataaatcat gaaggccact    420
atcatcctcc ttctgcttgc acaagtttcc tgggctggac cgtttcaaca gagaggctta    480
tttgacttta tgctagaaga tgaggcttct gggataggcc cagaagttcc tgatgaccgc    540
gacttcgagc cctccctagg cccagtgtgc cccttccgct gtcaatgcca tcttcgagtg    600
gtccagtgtt ctgatttggg tctggacaaa gtgccaaagg atcttccccc tgacacaact    660
ctgctagacc tgcaaaacaa caaaataacc gaaatcaaag atggagactt aagaacctg     720 aagaaccttc acgcattgat tcttgtcaac aataaaatta gcaaagttag tcctggagca    780
tttacacctt tggtgaagtt ggaacgactt tatctgtcca agaatcagct gaaggaattg    840
```

```
ccagaaaaaa tgcccaaaac tcttcaggag ctgcgtgccc atgagaatga gatcaccaaa      900
gtgcgaaaag ttactttcaa tggactgaac cagatgattg tcatagaact gggcaccaat      960
ccgctgaaga gctcaggaat tgaaaatggg gctttccagg gaatgaagaa gctctcctac     1020
atccgcattg ctgataccaa tatcaccagc attcctcaag gtcttcctcc ttcccttacg     1080
gaattacatc ttgatggcaa caaaatcagc agagttgatg cagctagcct gaaaggactg     1140
aataatttgg ctaagttggg attgagtttc aacagcatct ctgctgttga caatggctct     1200
ctggccaaca cgcctcatct gagggagctt cacttggaca caacaagct  taccagagta     1260 cctggtgggc tggcagagca taagtacatc caggttgtct accttcataa caacaatatc     1320
tctgtagttg atcaagtga cttctgccca cctggacaca caccaaaaa  ggcttcttat      1380 tcgggtgtga gtcttttcag caacccggtc cagtactggg agatacagcc atccaccttc     1440
agatgtgtct acgtgcgctc tgccattcaa ctcggaaact ataagtaatt ctcaagaaag     1500
ccctcatttt tataacctgg caaaatcttg ttaatgtcat tgctaaaaaa taaataaaag     1560
ctagatactg gaaacctaac tgcaatgtgg atgttttacc cacatgactt attatgcata     1620
aagccaaatt tccagtttaa gtaattgcct acaataaaaa gaaattttgc ctgccatttt     1680
cagaatcatc ttttgaagct ttctgttgat gttaactgag ctactagaga tattcttatt     1740
tcactaaatg taaaatttgg agtaaatata tatgtcaata tttagtaaag cttttctttt     1800
ttaatttcca ggaaaaaata aaagagtat  gagtcttctg taattcattg agcagttagc     1860
tcatttgaga taaagtcaaa tgccaaacac tagctctgta ttaatcccca tcattactgg     1920
taaagcctca tttgaatgtg tgaattcaat acaggctatg taaaattttt actaatgtca     1980 ttatttgaa  aaaataaatt taaaaataca ttcaaaatta ctattgtata caagcttaat     2040
tgttaatatt ccctaaacac aattttatga agggagaaga cattggtttg ttgacaataa     2100
cagtacatct tttcaagttc tcagctattt cttctacctc tccctatctt acatttgagt     2160
atggtaactt atgtcatcta tgttgaatgt aagcttataa agcacaaagc atacatttcc     2220
tgactggtct agagaactga tgtttcaatt taccccctctg ctaaataaat attaaaacta     2280
tcatgtgaaa aaaaaaaaaa aaaaa                                           2305
```

```
<210> SEQ ID NO 9
<211> LENGTH: 2151
<212> TYPE: DNA
<213> ORGANISM: artificial sequence
<220> FEATURE:
<223> OTHER INFORMATION: variant A2 human CN

<400> SEQUENCE: 9
ggaataataa gacacgccct gaaggagtac atcgtctagt gagggacaga ccaagcacgc       60
aaaacaaatt gcaatataat gtgataagtt ctttaaaaga ggtaagagca acgtgctttg      120
ggagcagaga agagggagaa agcagcatct tgcctggatg agccagggga cacagaagag      180
aagcccacta tctcatttaa tctttacaac tctcttgcaa ggttccctgg ttgtgaaaat      240
acatgagata aatcatgaag gccactatca tcctccttct gcttgcacaa gtttcctggg      300
ctggaccgtt tcaacagaga ggcttatttg actttatgct agaagatgag gcttctggga      360
taggcccaga agttcctgat gaccgcgact tcgagccctc cctaggccca gtgtgcccct      420
tccgctgtca atgccatctt cgagtggtcc agtgttctga tttgggtctg gacaaagtgc      480
caaaggatct tccccctgac acaactctgc tagacctgca aaacaacaaa ataaccgaaa      540
tcaaagatgg agactttaag aacctgaaga accttcacgc attgattctt gtcaacaata      600
```

-continued

| | |
|---|---|
| aaattagcaa agttagtcct ggagcattta cacctttggt gaagttggaa cgactttatc | 660 |
| tgtccaagaa tcagctgaag gaattgccag aaaaaatgcc caaaactctt caggagctgc | 720 |
| gtgcccatga aatgagatc accaaagtgc gaaaagttac tttcaatgga ctgaaccaga | 780 |
| tgattgtcat agaactgggc accaatccgc tgaagagctc aggaattgaa atggggctt | 840 |
| tccagggaat gaagaagctc tcctacatcc gcattgctga taccaatatc accagcattc | 900 |
| ctcaaggtct tcctccttcc cttacggaat tacatcttga tggcaacaaa atcagcagag | 960 |
| ttgatgcagc tagcctgaaa ggactgaata atttggctaa gttgggattg agtttcaaca | 1020 |
| gcatctctgc tgttgacaat ggctctctgg ccaacacgcc tcatctgagg gagcttcact | 1080 |
| tggacaacaa caagcttacc agagtacctg gtgggctggc agagcataag tacatccagg | 1140 |
| ttgtctacct tcataacaac aatatctctg tagttggatc aagtgacttc tgcccacctg | 1200 |
| gacacaacac caaaaaggct tcttattcgg gtgtgagtct tttcagcaac ccggtccagt | 1260 |
| actgggagat acagccatcc accttcagat gtgtctacgt gcgctctgcc attcaactcg | 1320 |
| gaaactataa gtaattctca agaaagccct catttttata acctggcaaa atcttgttaa | 1380 |
| tgtcattgct aaaaaataaa taaaagctag atactggaaa cctaactgca atgtggatgt | 1440 |
| tttacccaca tgacttatta tgcataaagc caaatttcca gtttaagtaa ttgcctacaa | 1500 |
| taaaaagaaa ttttgcctgc cattttcaga atcatctttt gaagctttct gttgatgtta | 1560 |
| actgagctac tagagatatt cttatttcac taaatgtaaa atttggagta aatatatatg | 1620 |
| tcaatattta gtaaagcttt tctttttttaa tttccaggaa aaaataaaaa gagtatgagt | 1680 |
| cttctgtaat tcattgagca gttagctcat ttgagataaa gtcaaatgcc aaacactagc | 1740 |
| tctgtattaa tccccatcat tactggtaaa gcctcatttg aatgtgtgaa ttcaatacag | 1800 |
| gctatgtaaa attttactta atgtcattat tttgaaaaaa taaatttaaa aatacattca | 1860 |
| aaattactat tgtatacaag cttaattgtt aatattccct aaacacaatt ttatgaaggg | 1920 |
| agaagacatt ggtttgttga caataacagt acatcttttc aagttctcag ctatttcttc | 1980 |
| tacctctccc tatcttacat ttgagtatgg taacttatgt catctatgtt gaatgtaagc | 2040 |
| ttataaagca caaagcatac atttcctgac tggtctagag aactgatgtt tcaatttacc | 2100 |
| cctctgctaa ataaatatta aaactatcat gtgaaaaaaa aaaaaaaaa a | 2151 |

<210> SEQ ID NO 10
<211> LENGTH: 1570
<212> TYPE: DNA
<213> ORGANISM: artificial sequence
<220> FEATURE:
<223> OTHER INFORMATION: Variant B human DCN

<400> SEQUENCE: 10

| | |
|---|---|
| atgaaggcca ctatcatcct ccttctgctt gcacaagttt cctgggctgg accgtttcaa | 60 |
| cagagaggct tatttgactt tatgctagaa gatgaggctt ctgggatagg cccagaagtt | 120 |
| cctgatgacc gcgacttcga gccctcccta ggcccagtgt gccccttccg ctgtcaatgc | 180 |
| catcttcgag tggtccagtg ttctgatttg gaactgggca ccaatccgct gaagagctca | 240 |
| ggaattgaaa tgggggcttt ccagggaatg aagaagctct cctacatccg cattgctgat | 300 |
| accaatatca ccagcattcc tcaaggtctt cctccttccc ttacggaatt acatcttgat | 360 |
| ggcaacaaaa tcagcagagt tgatgcagct agcctgaaag gactgaataa tttggctaag | 420 |
| ttgggattga gtttcaacag catctctgct gttgacaatg gctctctggc caacacgcct | 480 |
| catctgaggg agcttcactt ggacaacaac aagcttacca gagtacctgg tgggctggca | 540 |

-continued

| | |
|---|---|
| gagcataagt acatccaggt tgtctacctt cataacaaca atatctctgt agttggatca | 600 |
| agtgacttct gcccacctgg acacaacacc aaaaaggctt cttattcggg tgtgagtctt | 660 |
| ttcagcaacc cggtccagta ctgggagata cagccatcca ccttcagatg tgtctacgtg | 720 |
| cgctctgcca ttcaactcgg aaactataag taattctcaa gaaagccctc attttataa | 780 |
| cctggcaaaa tcttgttaat gtcattgcta aaaataaat aaaagctaga tactggaaac | 840 |
| ctaactgcaa tgtggatgtt tacccacat gacttattat gcataaagcc aaatttccag | 900 |
| tttaagtaat tgcctacaat aaaagaaat tttgcctgcc attttcagaa tcatcttttg | 960 |
| aagctttctg ttgatgttaa ctgagctact agagatattc ttatttcact aaatgtaaaa | 1020 |
| tttggagtaa atatatatgt caatatttag taaagctttt cttttttaat ttccaggaaa | 1080 |
| aaataaaaag agtatgagtc ttctgtaatt cattgagcag ttagctcatt tgagataaag | 1140 |
| tcaaatgcca aacactagct ctgtattaat ccccatcatt actggtaaag cctcatttga | 1200 |
| atgtgtgaat tcaatacagg ctatgtaaaa ttttactaa tgtcattatt ttgaaaaaat | 1260 |
| aaatttaaaa atacattcaa aattactatt gtatacaagc ttaattgtta atattcccta | 1320 |
| aacacaattt tatgaaggga gaagacattg gtttgttgac aataacagta catcttttca | 1380 |
| agttctcagc tatttcttct acctctccct atcttacatt tgagtatggt aacttatgtc | 1440 |
| atctatgttg aatgtaagct tataaagcac aaagcataca tttcctgact ggtctagaga | 1500 |
| actgatgttt caatttaccc ctctgctaaa taaatattaa aactatcatg tgaaaaaaaa | 1560 |
| aaaaaaaaaa | 1570 |

<210> SEQ ID NO 11
<211> LENGTH: 1456
<212> TYPE: DNA
<213> ORGANISM: artificial sequence
<220> FEATURE:
<223> OTHER INFORMATION: variant C human DCN

<400> SEQUENCE: 11

| | |
|---|---|
| atgaaggcca ctatcatcct ccttctgctt gcacaagttt cctgggctgg accgtttcaa | 60 |
| cagagaggct tatttgactt tatgctagaa gatgaggctc tgggatagg cccagaagtt | 120 |
| cctgatgacc gcgacttcga gccctcccta ggcccagtgt gccccttccg ctgtcaatgc | 180 |
| catcttcgag tggtccagtg ttctgatttg ggtcttcctc cttcccttac ggaattacat | 240 |
| cttgatggca acaaaatcag cagagttgat gcagctagcc tgaaaggact gaataatttg | 300 |
| gctaagttgg gattgagttt caacagcatc tctgctgttg acaatggctc tctggccaac | 360 |
| acgcctcatc tgagggagct tcacttggac aacaacaagc ttaccagagt acctggtggg | 420 |
| ctggcagagc ataagtacat ccaggttgtc taccttcata caacaatat ctctgtagtt | 480 |
| ggatcaagtg acttctgccc acctggacac aaccaaaa aggcttctta ttcgggtgtg | 540 |
| agtcttttca gcaacccggt ccagtactgg gagatacagc catccacctt cagatgtgtc | 600 |
| tacgtgcgct ctgccattca actcggaaac tataagtaat tctcaagaaa gccctcattt | 660 |
| ttataacctg gcaaaatctt gttaatgtca ttgctaaaaa ataaataaaa gctagatact | 720 |
| ggaaacctaa ctgcaatgtg gatgttttac ccacatgact tattatgcat aaagccaaat | 780 |
| ttccagttta agtaattgcc tacaataaaa agaaattttg cctgccattt tcagaatcat | 840 |
| cttttgaagc tttctgttga tgttaactga gctactagag atattcttat ttcactaaat | 900 |
| gtaaaatttg gagtaaatat atatgtcaat atttagtaaa gcttttcttt tttaattcc | 960 |
| aggaaaaaat aaaaagagta tgagtcttct gtaattcatt gagcagttag ctcatttgag | 1020 |

-continued

| | |
|---|---|
| ataaagtcaa atgccaaaca ctagctctgt attaatcccc atcattactg gtaaagcctc | 1080 |
| atttgaatgt gtgaattcaa tacaggctat gtaaaatttt tactaatgtc attatttga | 1140 |
| aaaaataaat ttaaaaatac attcaaaatt actattgtat acaagcttaa ttgttaatat | 1200 |
| tccctaaaca caattttatg aagggagaag acattggttt gttgacaata acagtacatc | 1260 |
| ttttcaagtt ctcagctatt tcttctacct ctccctatct tacatttgag tatggtaact | 1320 |
| tatgtcatct atgttgaatg taagcttata aagcacaaag catacatttc ctgactggtc | 1380 |
| tagagaactg atgtttcaat ttacccctct gctaaataaa tattaaaact atcatgtgaa | 1440 |
| aaaaaaaaaa aaaaaa | 1456 |

<210> SEQ ID NO 12
<211> LENGTH: 1336
<212> TYPE: DNA
<213> ORGANISM: Artificial sequence
<220> FEATURE:
<223> OTHER INFORMATION: variant D human DCN

<400> SEQUENCE: 12

| | |
|---|---|
| atgaaggcca ctatcatcct ccttctgctt gcacaagttt cctgggctgg accgtttcaa | 60 |
| cagagaggct tatttgactt tatgctagaa gatgaaggct ctgggatagg cccagaagtt | 120 |
| cctgatgacc gcgacttcga gccctcccta ggcccagtgt gccccttccg ctgtcaatgc | 180 |
| catcttcgag tggtccagtg ttctgatttg ggtctgaca aagtgccaaa ggatcttccc | 240 |
| cctgacacaa ctctgctaga cctgcaaaac aacaaaataa ccgaaatcaa agatggagac | 300 |
| tttaagaacc tgaagaacct tcacgttgtc taccttcata caacaatat ctctgtagtt | 360 |
| ggatcaagtg acttctgccc acctggacac aacaccaaaa aggcttctta ttcgggtgtg | 420 |
| agtcttttca gcaacccggt ccagtactgg gagatacagc catccacctt cagatgtgtc | 480 |
| tacgtgcgct ctgccattca actcggaaac tataagtaat tctcaagaaa gccctcattt | 540 |
| ttataacctg gcaaaatctt gttaatgtca ttgctaaaaa ataaataaaa gctagatact | 600 |
| ggaaacctaa ctgcaatgtg atgtttttac ccacatgact tattatgcat aaagccaaat | 660 |
| ttccagttta agtaattgcc tacaataaaa agaaattttg cctgccattt tcagaatcat | 720 |
| cttttgaagc tttctgttga tgttaactga gctactagag atattcttat ttcactaaat | 780 |
| gtaaatttg gagtaaatat atatgtcaat atttagtaaa gcttttcttt tttaatttcc | 840 |
| aggaaaaaat aaaagagta tgagtcttct gtaattcatt gagcagttag ctcatttgag | 900 |
| ataaagtcaa atgccaaaca ctagctctgt attaatcccc atcattactg gtaaagcctc | 960 |
| atttgaatgt gtgaattcaa tacaggctat gtaaaatttt tactaatgtc attatttga | 1020 |
| aaaaataaat ttaaaaatac attcaaaatt actattgtat acaagcttaa ttgttaatat | 1080 |
| tccctaaaca caattttatg aagggagaag acattggttt gttgacaata acagtacatc | 1140 |
| ttttcaagtt ctcagctatt tcttctacct ctccctatct tacatttgag tatggtaact | 1200 |
| tatgtcatct atgttgaatg taagcttata aagcacaaag catacatttc ctgactggtc | 1260 |
| tagagaactg atgtttcaat ttacccctct gctaaataaa tattaaaact atcatgtgaa | 1320 |
| aaaaaaaaaa aaaaaa | 1336 |

<210> SEQ ID NO 13
<211> LENGTH: 1223
<212> TYPE: DNA
<213> ORGANISM: Artificial sequence
<220> FEATURE:
<223> OTHER INFORMATION: Variant E human DCN

<400> SEQUENCE: 13

```
atgaaggcca ctatcatcct ccttctgctt gcacaagttt cctgggctgg accgtttcaa      60
cagagaggct tatttgactt tatgctagaa gatgaggctt ctgggatagg cccagaagtt     120
cctgatgacc gcgacttcga gccctccta ggcccagtgt gccccttccg ctgtcaatgc      180
catcttcgag tggtccagtg ttctgatttg ggttgtctac cttcataaca acaatatctc     240
tgtagttgga tcaagtgact tctgcccacc tggacacaac accaaaaagg cttcttattc     300
gggtgtgagt cttttcagca acccggtcca gtactgggag atacagccat ccaccttcag     360
atgtgtctac gtgcgctctg ccattcaact cggaaactat aagtaattct caagaaagcc     420
ctcatttta taacctggca aaatcttgtt aatgtcattg ctaaaaaata aataaaagct      480
agatactgga aacctaactg caatgtggat gttttaccca catgacttat tatgcataaa     540
gccaaatttc cagtttaagt aattgcctac aataaaaaga aattttgcct gccattttca     600
gaatcatctt ttgaagcttt ctgttgatgt taactgagct actagagata ttcttatttc     660
actaaatgta aaatttggag taaatatata tgtcaatatt tagtaaagct tttctttttt     720
aatttccagg aaaaaataaa aagagtatga gtcttctgta attcattgag cagttagctc     780
atttgagata aagtcaaatg ccaaacacta gctctgtatt aatccccatc attactggta     840
aagcctcatt tgaatgtgtg aattcaatac aggctatgta aaattttac taatgtcatt      900
attttgaaaa aataaattta aaaatacatt caaaattact attgtataca agcttaattg     960
ttaatattcc ctaaacacaa ttttatgaag ggagaagaca ttggtttgtt gacaataaca    1020
gtacatcttt tcaagttctc agctatttct tctacctctc cctatcttac atttgagtat    1080
ggtaacttat gtcatctatg ttgaatgtaa gcttataaag cacaaagcat acatttcctg    1140
actggtctag agaactgatg tttcaattta ccctctgct aaataaatat taaaactatc    1200
atgtgaaaaa aaaaaaaaaa aaa                                            1223
```

<210> SEQ ID NO 14
<211> LENGTH: 1065
<212> TYPE: DNA
<213> ORGANISM: Artificial sequence
<220> FEATURE:
<223> OTHER INFORMATION: Murine DCN

<400> SEQUENCE: 14

```
atgaaggcaa ctctcatctt cttccttctg gcacaagtct cttgggctgg accatttgaa      60
cagagaggct tatttgactt catgctagaa gatgaggctt ctggcataat cccttatgac     120
cctgacaatc ccctgatatc tatgtgcccc taccgatgcc agtgtcatct tcgagtggtg     180
cagtgttctg atctgggttt ggacaaagtg ccctgggatt ttccacccga cacaaccttg     240
ctagacctgc aaaacaacaa aattacagag atcaaagaag gggccttcaa gaacctgaag     300
gacttgcata ccttgatcct tgtcaacaac aagatcagca aaatcagtcc agaggcattc     360
aaacctctcg tgaagttgga aaggctttac ctgtctaaga ccaactaaa ggaactgcct      420
gaaaaaatgc ccagaactct ccaggaactt cgtgtccatg agaatgagat caccaagctg     480
cggaaatccg acttcaatgg actgaacaat gtgcttgtca tagaactggg cggcaaccca    540
ctgaaaaact ctgggattga aacggagcc ttccagggac tgaagagtct ctcatacatt     600
cgcatctcag acaccaacat aactgcgatc cctcaaggtc tgcctacttc tctcactgaa     660
gtgcatctag atggcaacaa gatcaccaag gttgatgcac ccagcctgaa aggactgatt    720
aatttgtcta aactgggatt gagcttcaac agcatcaccg ttatggagaa tggcagtctg    780
```

```
gccaatgttc ctcatctgag ggaactccac ttggacaaca acaaactcct cagggtgcct    840
gctgggctgg cacagcataa gtatatccag gtcgtctacc ttcacaacaa caacatctcc    900
gcagttgggc aaaatgactt ctgccgagct ggacacccct ctcgaaaggc ttcctactcg    960
gctgtgagtc tttacggcaa ccctgtccgg tattgggaaa tctttccaaa caccttcaga   1020
tgtgtctatg tgcgttctgc cattcaactt ggaaactaca agtaa                   1065

<210> SEQ ID NO 15
<211> LENGTH: 30
<212> TYPE: PRT
<213> ORGANISM: artificial sequence
<220> FEATURE:
<223> OTHER INFORMATION: murine 42-71 DCN

<400> SEQUENCE: 15

Asp Asn Pro Leu Ile Ser Met Cys Pro Tyr Arg Cys Gln Cys His Leu
1               5                  10                  15

Arg Val Val Gln Cys Ser Asp Leu Gly Leu Asp Lys Val Pro
            20                  25                  30

<210> SEQ ID NO 16
<211> LENGTH: 41
<212> TYPE: PRT
<213> ORGANISM: artificial sequence
<220> FEATURE:
<223> OTHER INFORMATION: human DCN fragment

<400> SEQUENCE: 16

Ile Gly Pro Glu Val Pro Asp Asp Arg Asp Phe Glu Pro Ser Leu Gly
1               5                  10                  15

Pro Val Cys Pro Phe Arg Cys Gln Cys His Leu Arg Val Val Gln Cys
            20                  25                  30

Ser Asp Leu Gly Leu Asp Lys Val Pro
            35                  40
```